(12) United States Patent
Clark et al.

(10) Patent No.: US 9,144,460 B2
(45) Date of Patent: Sep. 29, 2015

(54) CATHETER WITH DIRECT COOLING ON NONABLATING ELEMENT

(71) Applicant: Biosense Webster (Israel), Ltd., Yokneam (IL)

(72) Inventors: Jeffrey L. Clark, Castaic, CA (US); Michael D. Banando, Glendora, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 313 days.

(21) Appl. No.: 13/732,297

(22) Filed: Dec. 31, 2012

(65) Prior Publication Data

US 2014/0188104 A1 Jul. 3, 2014

(51) Int. Cl.
*A61B 18/14* (2006.01)
*A61B 18/00* (2006.01)
*A61B 17/00* (2006.01)
*A61M 25/01* (2006.01)
*A61B 19/00* (2006.01)

(52) U.S. Cl.
CPC ......... *A61B 18/1492* (2013.01); *A61B 19/5244* (2013.01); *A61B 2017/003* (2013.01); *A61B 2017/00318* (2013.01); *A61B 2018/00011* (2013.01); *A61B 2018/00029* (2013.01); *A61B 2018/00357* (2013.01); *A61B 2018/00577* (2013.01); *A61B 2018/00821* (2013.01); *A61B 2018/147* (2013.01); *A61B 2218/002* (2013.01); *A61M 2025/015* (2013.01)

(58) Field of Classification Search
CPC ...................... A61B 18/1492; A61B 2218/002; A61B 5/042; A61B 2018/00011
USPC .......................................................... 606/41
See application file for complete search history.

(56) References Cited

U.S. PATENT DOCUMENTS

| 5,643,197 | A | 7/1997 | Brucker et al. | |
|---|---|---|---|---|
| 5,964,757 | A | 10/1999 | Ponzi | |
| 6,053,912 | A | 4/2000 | Panescu et al. | |
| 6,171,275 | B1 * | 1/2001 | Webster, Jr. | 604/20 |
| 6,605,087 | B2 | 8/2003 | Swartz et al. | |
| 6,611,699 | B2 | 8/2003 | Messing | |

(Continued)

FOREIGN PATENT DOCUMENTS

| EP | 1 690 510 A1 | 8/2006 |
|---|---|---|
| EP | 2 382 935 A1 | 11/2011 |
| WO | WO 2011/115787 A1 | 9/2011 |

OTHER PUBLICATIONS

Extended European Search Report dated Mar. 27, 2014 in EP Application No. 13199550.8 (7 pages).

*Primary Examiner* — Catherine Voorhees
(74) *Attorney, Agent, or Firm* — Christie, Parker & Hale, LLP

(57) ABSTRACT

A catheter tip electrode has a tissue contacting surface which electrically conducts RF energy to the tissue and is more thermally conductive than adjacent non-electrically conductive coating or cover which prevents RF conduction to the tissue contacting that surface. The tip electrode has a shell with a nonablating hollow proximal neck portion and a distal ablating portion defining a fluid chamber, and a plug-like support member which is configured with a fluid channel on its outer surface so a fluid passage is provided between the member and the neck portion for convective or direct cooling of the nonablating neck portion and nonconductive tubing covering it.

18 Claims, 7 Drawing Sheets

(56) References Cited

U.S. PATENT DOCUMENTS

| | | |
|---|---|---|
| 6,764,487 B2 | 7/2004 | Mulier et al. |
| 7,217,268 B2 | 5/2007 | Eggers et al. |
| 7,276,061 B2 | 10/2007 | Schaer et al. |
| 7,819,866 B2 | 10/2010 | Bednarek |
| 2008/0255540 A1 | 10/2008 | Selkee |
| 2009/0005768 A1* | 1/2009 | Sharareh et al. ............... 606/17 |
| 2009/0093810 A1* | 4/2009 | Subramaniam et al. ........ 606/41 |
| 2010/0137851 A1 | 6/2010 | Lin et al. |
| 2010/0168728 A1 | 7/2010 | Wang et al. |
| 2010/0168827 A1 | 7/2010 | Schultz |
| 2011/0270244 A1 | 11/2011 | Clark et al. |
| 2013/0317375 A1* | 11/2013 | Garcia et al. ................ 600/508 |
| 2014/0163548 A1* | 6/2014 | Christian ...................... 606/41 |

\* cited by examiner

CATHETER WITH DIRECT COOLING ON NONABLATING ELEMENT

FIELD OF INVENTION

The present invention relates to catheters that have an active distal portion, including an irrigated tip electrode, particularly useful for ablating heart tissue.

BACKGROUND OF INVENTION

Ablation of cardiac tissue is well known as a treatment for cardiac arrhythmias. In radio-frequency (RF) ablation, for example, a catheter is inserted into the heart and brought into contact with tissue at a target location. RF energy is then applied through electrodes on the catheter to heat tissue to a destructive temperature in order to create a lesion for the purpose of breaking arrhythmogenic current paths in the tissue.

Irrigated catheters are now commonly used in ablation procedures. Open-loop irrigation provides many benefits including cooling of the electrode and tissue which prevents overheating of tissue that can otherwise cause adjacent blood to form char and coagulum. Despite efficient cooling of the electrode tip, under certain circumstances, adjacent catheter tip structures are heated by the tissue lesion site and the formation of coagulum and/or char can occur on these structures which are typically formed from a non-electrically conductive elastomer or plastic. The historic mode of operation relies on a scavenging effect where the tip electrode cooling fluid also cools these adjacent structures to some degree. However, it is desirable for an irrigated ablation catheter to prevent the formation of char and/or coagulum on adjacent, non-ablating tip structures and surfaces by convective and direct cooling.

Accordingly, it is desirable that an irrigated ablation catheter provide efficient cooling of adjoining non-ablating catheter tip structures which, due to their close proximity, are heated by the tissue lesion site.

SUMMARY OF THE INVENTION

The present invention seeks to minimize, if not prevent, the formation of char and/or coagulum on adjacent structures of an irrigated ablation tip electrode by convectively or directly cooling these structures. A catheter is constructed with an electrically conductive tip which has the benefit of being more thermally conductive than nonconductive or elastomeric structures to which it is bonded. The electrode tip has a tissue contacting surface which electrically conducts RF energy to the tissue. The tip has an adjacent surface which is coated or covered with a non-electrically conductive material and such, prevents RF conduction to the tissue contacting that surface. With thermally conductive substrate electrode underneath the non-electrically conductive material, the nonablating surface can be cooled by porting to effectively scavenge some of the irrigation flow through the tip electrode to the non-ablating surface.

Accordingly, the present invention is directed to a catheter having an elongated catheter body and a tip electrode with a shell, an internal support member, and an elastomeric tubing wherein the shell has a neck and a chamber, and the support member has a proximal portion inserted in the neck of the shell and a distal portion extending into the chamber of the shell. The proximal portion has a fluid through-hole which is in communication with a fluid channel provided between the neck of the shell and the proximal portion of the support member to define a fluid passage between the fluid through-hole and the chamber for cooling the neck of the shell and hence cooling at least a portion of the tubing covering the neck to minimize formation of char and coagulum thereon. In a more detailed embodiment, the fluid channel is helical along an outer surface of the proximal portion to maximize surface area exposure of the neck to irrigation fluid for convective cooling.

In another embodiment, the fluid channel has axial and radial branches to pass fluid to the chamber and to irrigation ports provided in the neck of the shell and a nonconductive tubing of the distal section covering the shell. The irrigation ports allow fluid to pass to the outside of the tip electrode to directly cool the nonablating areas of the tip electrode.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
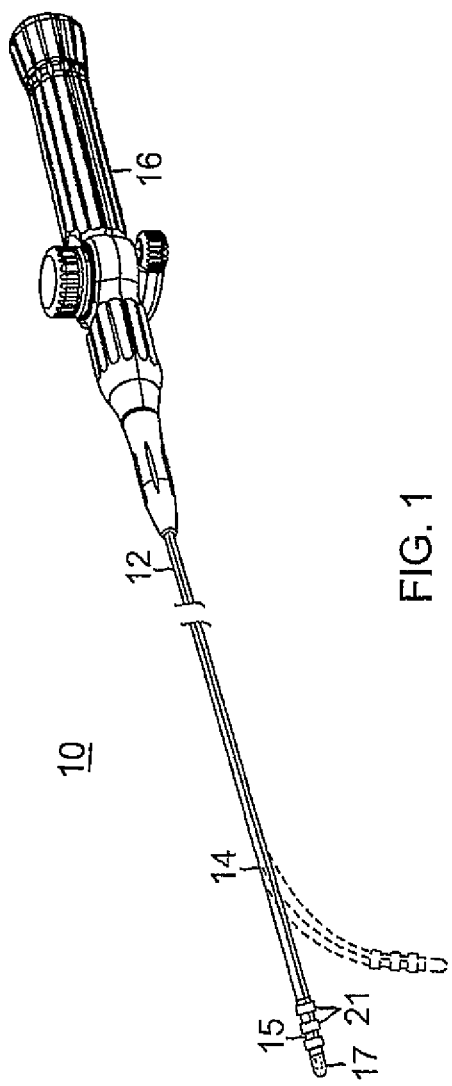
FIG. 1 is a perspective view of a catheter in accordance with an embodiment of the present invention.

FIG. 1 illustrates an embodiment of a catheter 10 with an irrigated ablation tip electrode that provides efficient, direct cooling of adjoining non-ablating catheter tip structures, which due to their close proximity, are heated by the tissue lesion site. The catheter has an elongated catheter body 12 with proximal and distal ends, an intermediate deflectable section 14 at the distal end of the catheter body 12, and a distal section 15 with a tip electrode 17 adapted for ablation with direct irrigated cooling. The catheter also includes a control handle 16 at the proximal end of the catheter body 12 for controlling deflection (single or bi-directional) of the intermediate section 14 relative to the catheter body 12.

Figure 2A:
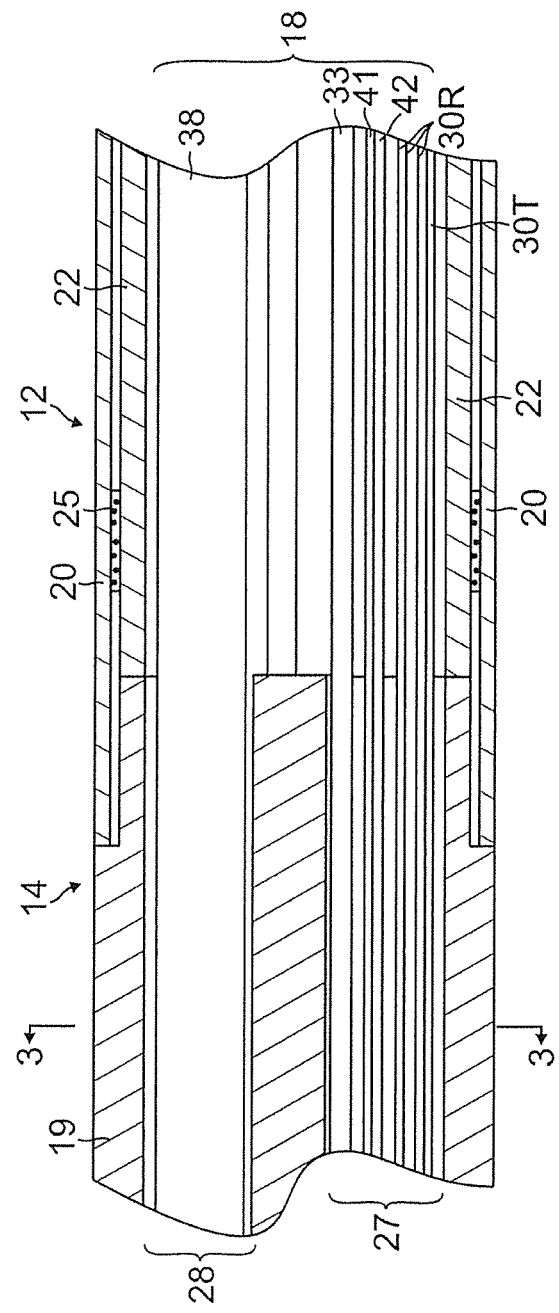
FIG. 2A is a side cross-sectional view of the catheter of FIG. 1, including a junction between a catheter body and a deflectable intermediate section, taken along a first diameter.
Figure 2B:
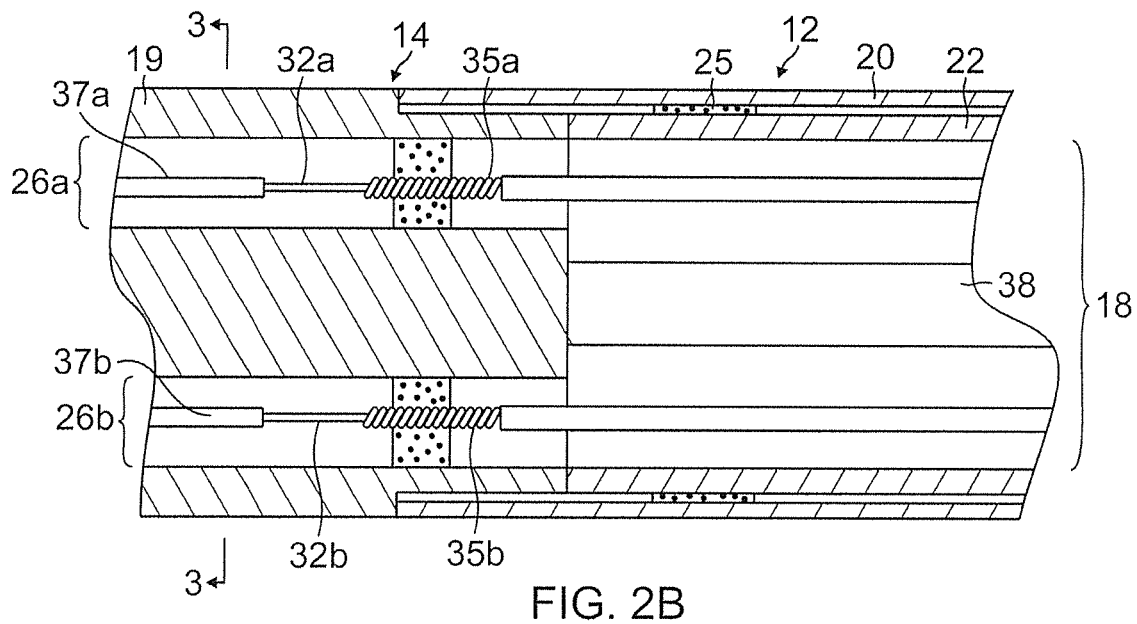
FIG. 2B is a side cross-sectional view of the catheter of FIG. 1, including a junction between a catheter body and a deflectable intermediate section, taken along a second diameter generally orthogonal to the first diameter of FIG. 2A.

With reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate puller members (e.g., puller wires), lead wires, and any other desired wires, cables or tubings. If desired, the inner surface of the outer wall 20 is lined with a stiffening tube 22 to provide improved torsional stability. A disclosed embodiment, the catheter has an outer wall 20 with an outer diameter of from about 0.090 inch to about 0.94 inch and an inner diameter of from about 0.061 inch to about 0.065 inch.

Distal ends of the stiffening tube 22 and the outer wall 20 are fixedly attached near the distal end of the catheter body 12 by forming a glue joint 25 with polyurethane glue or the like. A second glue joint (not shown) is formed between proximal ends of the stiffening tube 20 and outer wall 22 using a slower drying but stronger glue, e.g., polyurethane.

Components that extend between the control handle 16 and the deflectable section 14 pass through the central lumen 18 of the catheter body 12. These components include lead wires 30T and 30R for the tip electrode 17 and a plurality of ring electrodes 21 carried on the distal section 15, an irrigation tubing 38 for delivering fluid to the tip electrode, a cable 33 for an electromagnetic position sensor 34 carried in the distal section 15, puller wires 32a, 32b for deflecting the intermediate section 14, and a pair of thermocouple wires 41, 42 to sense temperature at the distal section 15.

Figure 3:
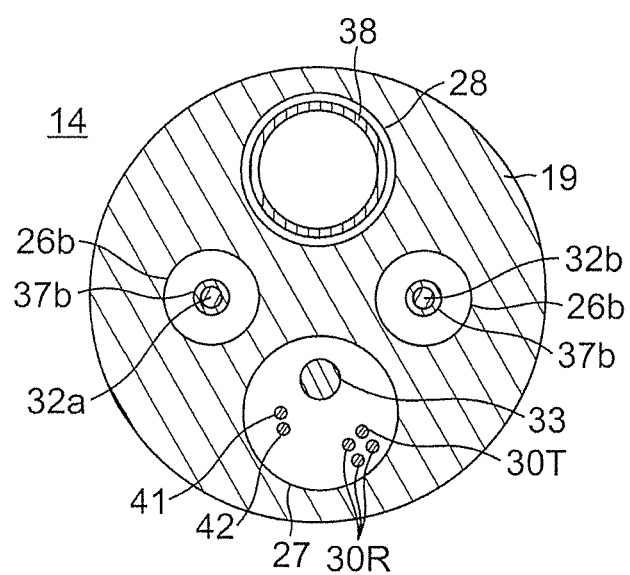
FIG. 3 is an end cross-sectional view of the intermediate section of FIGS. 2A and B, taken along line 3-3.

Illustrated in FIG. 2A, 2B and 3 is an embodiment of the intermediate section 14 which comprises a short section of tubing 19. The tubing also has a braided mesh construction but with multiple lumens, for example off-axis lumens 26a, 26b, 27, 28. The first lumen 26a carries a puller wire 32a for deflection of the intermediate section. For bi-directional deflection, the diametrically opposing second lumen 26b carries a second puller wire 32b. The third lumen 27 carries the lead wires 30T and 30R, the thermocouple wires 41 and 42, and the sensor cable 33. The fourth lumen 28 carries the irrigation tubing 38.

The tubing 19 of the intermediate section 14 is made of a suitable non-toxic material that is more flexible than the catheter body 12. A suitable material for the tubing 19 is braided polyurethane, i.e., polyurethane with an embedded mesh of braided stainless steel or the like. The size of each lumen is not critical, but is sufficient to house the respective components extending therethrough.

A means for attaching the catheter body 12 to the intermediate section 14 is illustrated in FIGS. 2A and 2B. The proximal end of the intermediate section 14 comprises an outer circumferential notch 25 that receives an inner surface of the outer wall 20 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Each puller wire 32a and 32b is preferably coated with Teflon® The puller wires can be made of any suitable metal, such as stainless steel or Nitinol and the Teflon coating imparts lubricity to the puller wire. The puller wire preferably has a diameter ranging from about 0.006 to about 0.010 inch.

As shown in FIG. 2B, portion of each puller wire in the catheter body 12 passes through a compression coil 35a or 35b in surrounding relation to its puller wire. Each compression coil 35a or 35b extends from the proximal end of the catheter body 12 to at or near the proximal end of the intermediate section 14. The compression coils are made of any suitable metal, preferably stainless steel, and are tightly wound on themselves to provide flexibility, i.e., bending, but to resist compression. The inner diameter of the compression coil is preferably slightly larger than the diameter of the puller wire. Within the catheter body 12, the outer surface of the compression coil 35a or 35b is also covered by a flexible, non-conductive sheath 39, e.g., made of polyimide tubing. Each portion of the puller wires distal of the compression coil 35a or 35b may extend through a respective protective sheath 37a or 37b to prevent the puller wire from cutting into the tubing 19 of the intermediate section 14 during deflection.

Proximal ends of the puller wires 32a and 32b are anchored in the control handle 16. Distal ends of the puller wires 32a and 32b are anchored in the distal section 15, as described further below. Separate and independent longitudinal movements of the puller wires relative to the catheter body 12, which results in, respectively, deflection of the intermediate section 14 along a plane, are accomplished by suitable manipulation of a deflection member of the control handle 16.

Suitable deflection members and/or deflection assemblies are described in co-pending U.S. Publication No. US2010/0168827 A1, published Jul. 1, 2010, entitled DEFLECTABLE SHEATH INTRODUCER, and U.S. Publication No. US2008/0255540 A1, published Oct. 16, 2008, entitled STEERING MECHANISM FOR BI-DIRECTIONAL CATHETER, the entire disclosures of both of which are hereby incorporated by reference.

Figure 4A:
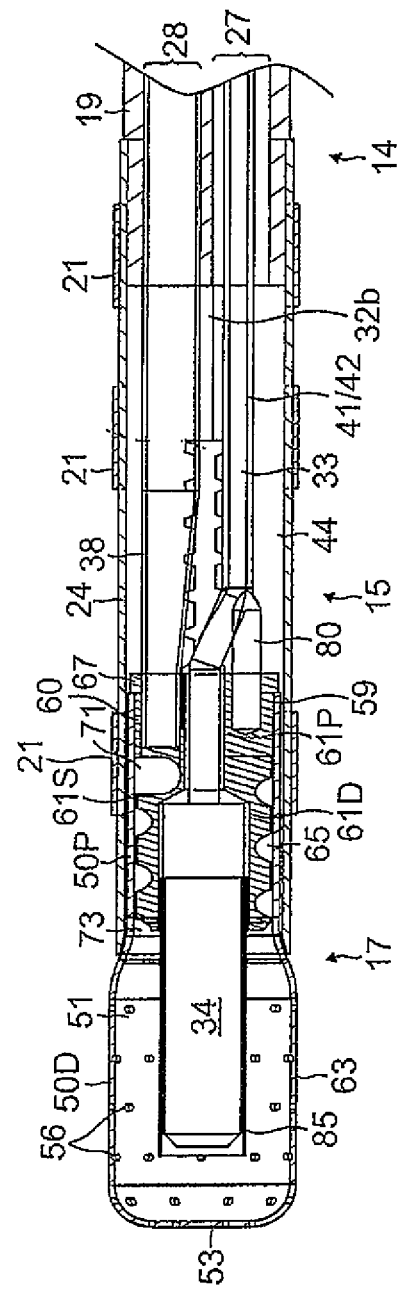
FIG. 4A is a side cross-sectional view of the catheter of FIG. 1, including a distal section 15, in accordance with an embodiment of the present invention.
Figure 4B:
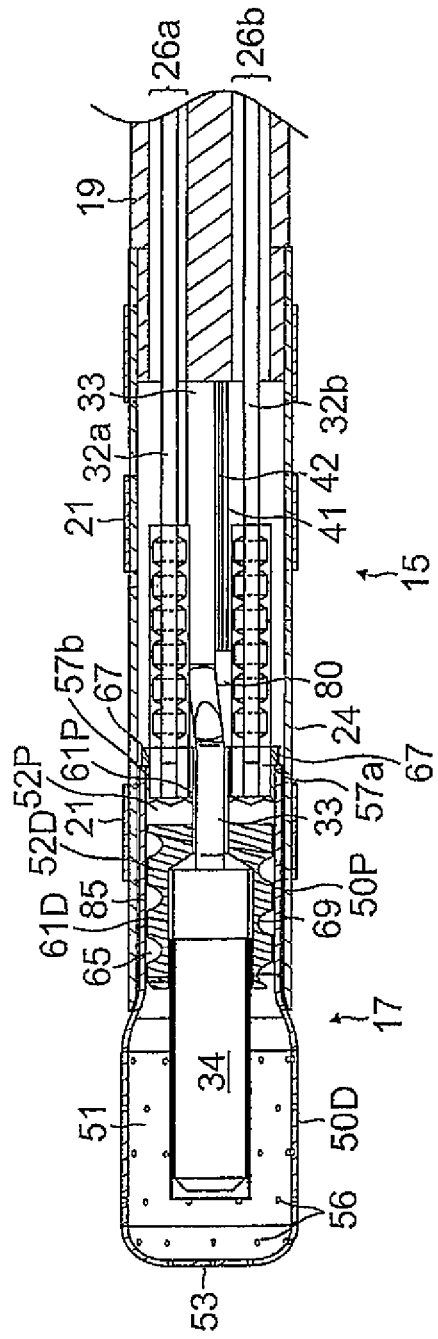
FIG. 4B is a top plan view of the distal section of FIG. 4A.

With reference to FIGS. 4A and 4B, at the distal end of the intermediate section 14 is the distal tip section 15 that includes the tip electrode 17 and a relatively short piece of non-conductive connector tubing or covering 24 between the tip electrode 17 and the intermediate section 14. In the illustrated embodiment, the connector tubing 24 has a single lumen 44 which houses the position sensor 34 and allows passage of components including electrode lead wires 30T and 30R, the sensor cable 33, thermocouple wires 41 and 42, and the irrigation tubing 38 into the distal section 15 and tip electrode 17. The single lumen 44 of the connector tubing 24 allows these components to reorient themselves as needed from their respective lumens in the intermediate section 14 toward their location within the distal section 15 and tip electrode 17. In the disclosed embodiment, the tubing 24 is a protective tubing, e.g., PEEK tubing, having a length ranging between 6 mm and 12 mm, more preferably about 11 mm.

Figure 5:
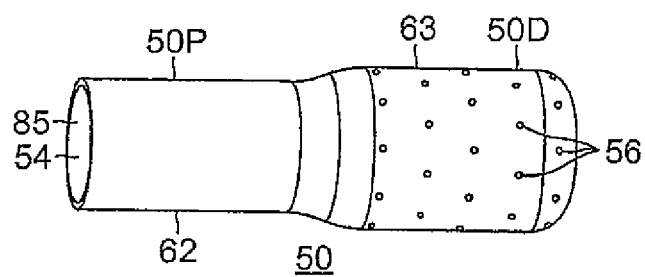
FIG. 5 is a perspective view of a shell of a tip electrode, in accordance with an embodiment of the present invention.
Figure 6A:
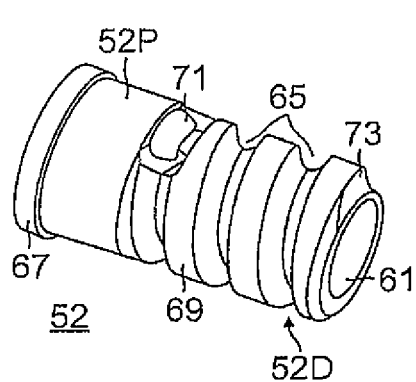
FIG. 6A is a perspective view of a support member of a tip electrode, in accordance with an embodiment of the present invention.
Figure 6B:
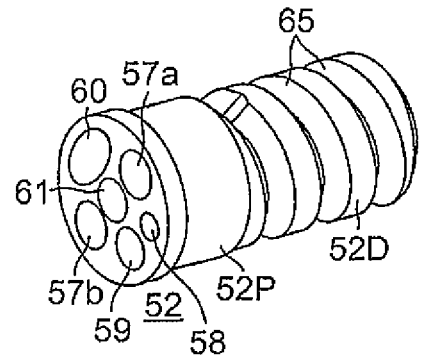
FIG. 6B is another perspective view of the support member of FIG. 6A.

The tip electrode 17 defines a longitudinal axis 46 and is of at least a two-piece configuration that includes an electrically conductive dome shell 50 as shown in FIG. 5 and an electrically conductive internal support member 52 as shown in FIGS. 6A and 6B, which jointly define a cavity or chamber 51 surrounded and enclosed by the shell 50 and the support member 52. The shell 50 has a electrically-conductive distal portion 50D adapted for contact with tissue for ablation and a nonablating proximal portion 50P. The distal portion 50D has a hollow tubular or cylindrical shape and a closed and rounded atraumatic distal end 53. The proximal portion 50P has a proximal hollow cylindrical neck portion 62 with an open proximal end 54 defined by a rim. Formed in shell wall 63 are a plurality of fluid ports 56 that allow fluid communication between the cavity 51 and outside the shell.

As shown in FIGS. 4A and 4B, the support member 52 forms a fluid-tight seal at the proximal end 54 of the shell 50. The support member 52 seals the interior cavity 51 of the shell 50, and the shell 50 and the support member 52 facilitate the provision of a plenum condition within the cavity; that is, where fluid is forced or delivered into it for a more uniform distribution through fluid ports 56 formed in shell wall 63.

With reference to FIGS. 6A and 6B, the support member 52 has a generally cylindrical body with a distal portion 52D and a proximal portion 52P. At a proximal end of the proximal portion 52P, a radial lip 67 is formed which engages with the rim of the shell 50. A proximal surface of the proximal portion 52P has a plurality of axial blind holes and axial through-holes. In the illustrated embodiment, the proximal surface has four blind holes, namely, 57a, 57b, 58 and 59, and two through-holes 60 and 61 The blind holes 57a and 57b are off-axis, diametrically opposed and in longitudinal alignment with the lumens 26a and 26b of the intermediate section 14 for receiving and anchoring distal ends of the puller wires 32a and 32b, respectively. The blind hole 58 is off-axis and in general longitudinal alignment with the lumen 27 of the intermediate section 14 for receiving and anchoring distal ends of the thermocouple wires 41 and 42. The blind hole 59 is off axis and in general longitudinal alignment with the lumen 27 of the intermediate section 14 for receiving and anchoring a distal end of the tip electrode lead wire 30T. The through hole 60 is off-axis and elliptical and in alignment with the lumen 28 of the intermediate section 14 for receiving and anchoring a distal end of the irrigation tubing 38. The through-hole 61 is on-axis and is in general alignment with the lumen of the intermediate section 14 for receiving a distal end of the sensor cable 33.

The through-hole 61 extends through the entire longitudinal length of the support member 52, through both the proximal portion 52P and the distal portion 52D, thus providing a passage through the support member 52. The passage of through-hole 61 has a proximal portion 61P with a small diameter, a distal portion 61D with a larger diameter forming a step 61 S therebetween. The distal portion 62D houses at least a proximal portion of the position sensor 34. A protective tubing 82 may be provided for a distal portion of the position sensor 34 extending into the chamber 51. The proximal portion 61P allows the sensor cable 33 to extend proximally from the sensor 34. A proximal end of the sensor 34 rests against the step 61S.

The through-hole 60 extends through proximal portion 52P and feeds into and connects with a fluid channel 65 formed in an outer circumferential surface 69 of the distal portion 52D. The channel 65 has a proximal opening 71 and a distal opening 73. In the illustrated embodiment, the channel 65 is a helical pattern (e.g., about three full loops or 1080 degrees) that extends along the length of the distal portion 52D and gives the distal portion an appearance of being "threaded". The proximal opening 71 communicates with the through-hole 60 and the distal opening communicates with the plenum chamber 51. Thus, the channel 65 provides fluid communication between the through-hole 61 and the chamber 51 along the outer surface 69 of the distal portion 52D.

With the support member 52 inserted in the shell 50 forming the tip electrode 17 as shown in FIGS. 4A and 4B, the channel 65 on the outer surface 69 of the distal portion 52D enables significant portions of an inner surface 85 of the neck 62 of the shell 50 lining the channel 65 to be directly exposed to irrigation fluid delivered by the irrigation tubing 38 to the irrigation through-hole 60. Thus, the neck 62 of the shell 50 is directly cooled by irrigation fluid, which in turn directly cools the connector tubing 24 so as to minimize the formation of char and coagulum on a non-ablating surface of the tip electrode 50.

It is understood that the channel 65 may assume a variety of shapes and patterns so long as it exposes the inner surface 85 of the shell 50 and its neck 62 to cooling irrigation fluid passed into the tip electrode via the through-hole 60. Direct cooling of the neck 62 effectively cools the connector tubing 24 of the distal section 15 covering the neck 62 of the shell 50 and minimizes the formation of char and coagulum on the nonconducting, nonablating surface of the tubing 24.

Figure 7A:
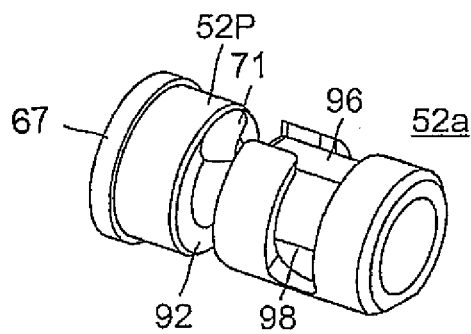
FIG. 7A is a perspective view of a support member, in accordance with another embodiment of the present invention.
Figure 7B:
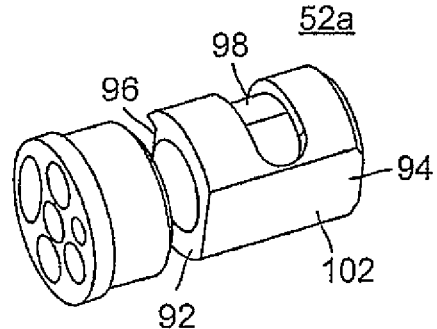
FIG. 7B is another perspective view of the support member of FIG. 7A.
Figure 8:
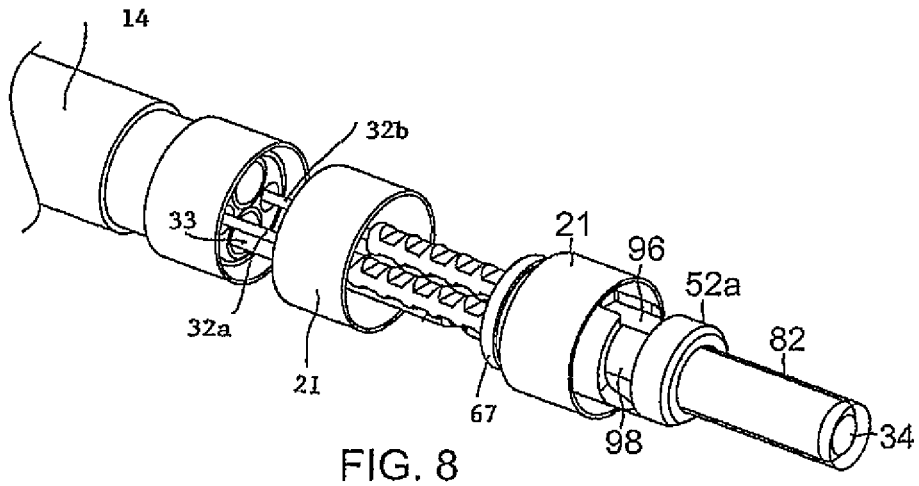
FIG. 8 is a perspective view of a distal section with the support member of FIG. 7A, with parts removed for better clarity, in accordance with another embodiment of the present invention.
Figure 9:
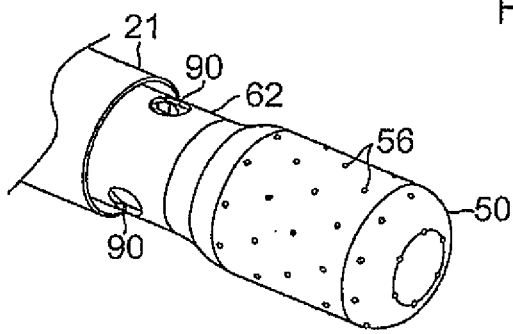
FIG. 9 is a perspective view of the distal section of FIG. 8, including a tip electrode shell with additional irrigated ports in a proximal neck portion.
Figure 10:
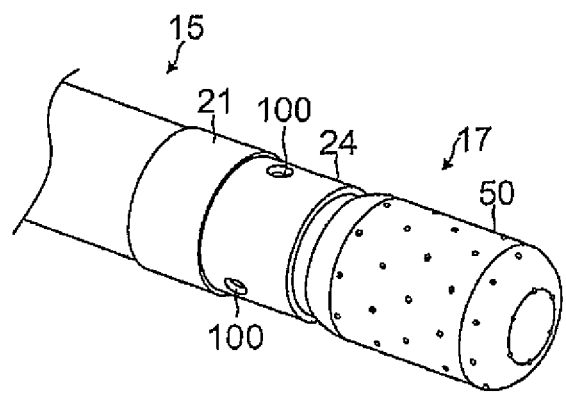
FIG. 10 is a perspective view of the distal section of FIG. 8, including a connector tubing with irrigated ports.

FIGS. 7A, 7B and 8 illustrate an alternate embodiment of the support member 52a with a dual feeder system with channel 65 having axial branches and radial branches. Proximal radial branch 92 feeds axial branch 94 which feeds into the chamber 51. Proximal radial branch 92 also feeds axial branch 96 which feeds distal radial branch 98. Distal radial branch 98 is in communication with irrigation ports 90 (FIG. 9) on the neck 62 of the electrode 50P which are aligned and in communication with irrigation ports 100 (FIG. 10) in the tubing 24. The ports 100 allow irrigation fluid to pass to the outside for directly cooling the nonconductive, nonablating neck 62.

The total hydraulic resistance (combined resistance of the ports as well as the branches) should be balanced between the branches that feed the neck 62 and those that feed the chamber 51 such that both zones of the tip are irrigated. This can be accomplished by varying the number and size of the fluid ports 56 of the shell 50. In one embodiment, the ports 56 have a diameter of about 0.0035 in. Additionally, the cross sectional area of the branches can be adjusted to increase or reduce the hydraulic resistance of any given branch. FIG. 7B shows the branch 94 feeding the chamber 51 having a "flat" surface 102 on the outer surface of the distal portion 52D of the support member 52. Varying the depth of the flat surface will inversely change the effective cross section of the branch 94. In a similar manner, the T shaped intersection of branches 92/96 and 96/98 can be varied in both width and depth to affect its hydraulic resistance. Varying the geometry of the feeder branches themselves provides an additional parameter for tuning the flow distribution between the neck and plenum zones beyond adjustment of the port sizes and numbers alone. As discussed in patent application Ser. No. 12/769,592 Clark et al, it is helpful to consider the Diffusion Ratio which is the sum total of the output area (irrigation ports) divided by the input area (fluid lumen cross section). In the case of the electrode with both conductive and non-conductive irrigated surfaces, it will be helpful to either reduce the number and size of irrigation ports or increase the diameter of the fluid lumen in order to preserve the overall diffusion ratio at approximately 2 or less, and more ideally at 1.3 or less.

The shell 50 and the support member 52 are constructed of a biocompatible metal, including a biocompatible metal alloy. A suitable biocompatible metal alloy includes an alloy selected from stainless steel alloys, noble metal alloys and/or combinations thereof. In one embodiment, the shell is constructed of an alloy comprising about 80% palladium and about 20% platinum by weight. In an alternate embodiment, the shell 50 and the member 52 are constructed of an alloy comprising about 90% platinum and about 10% iridium by weight. The shell can formed by deep-drawing manufacturing process which produces a sufficiently thin but sturdy shell wall that is suitable for handling, transport through the patient's body, and tissue contact during mapping and ablation procedures.

Distal ends of the thermocouple wires 41 and 42 may be covered in a nonconductive cover or sheath, for example, a polyester heat shrink sleeve. The sheath is an electrically insulating, second protective covering over the thermocouple wires (proximal to thermocouple junction 80) to prevent abrasion against the support member 52. Surrounding a distal portion of the sheath may be another nonconductive tubing, for example, a polyimide tubing. The tubing is constructed of a thermally conductive material which provides electrical isolation between the thenuocouple junction 80 and the support member 52 which is energized with RF potential.

In the illustrated embodiment, the sensor 34 and cable 33 are front-loaded into the support member 52 during assembly of the tip electrode 17. That is, before the shell 50 is mounted on the support member 52, the sensor 34 and its cable 33 are fed (proximal end of the cable first) into the through hole 61 from the distal end of the support member. A distal end of the tubing 82 covering the sensor 34 is filled and packed with a suitable adhesive so as to seal the tubing 82 against fluid leakage from the cavity 51. The shell 50 is then mounted on the support member 52 with the distal portion 52 extending into the cavity 51, the proximal portion 52D filling the neck 62 and the rim abutting against the lip 67. The rim and the lip are soldered to fixedly attach the shell 60 and the support member 52.

As shown in FIGS. 4A and 4B, ring electrodes 21 may be mounted on the connector tubing 24 of the distal section 15. They may be made of any suitable solid conductive material, such as platinum or gold, preferably a combination of platinum and iridium. The ring electrodes can be mounted onto the connector tubing 24 with glue or the like. Alternatively, the ring electrodes can be formed by coating the tubing 24 with an electrically conducting material, like platinum, gold and/or iridium. The coating can be applied using sputtering, ion beam deposition or an equivalent technique. The number of the ring electrodes on the tubing 24 can vary as desired. The rings may be monopolar or bi-polar. In the illustrated embodiment, there is a distal monopolar ring electrode and a proximal pair of bi-polar ring electrodes. Each ring electrode is connected to a respective lead wire 30R.

As understood by one of ordinary skill in the art, each lead wire 30R is attached to its corresponding ring electrode by any suitable method. A preferred method for attaching a lead wire to a ring electrode involves first making a small hole through the wall of the tubing 24. Such a hole can be created, for example, by inserting a needle through the non-conductive covering and heating the needle sufficiently to form a permanent hole. The lead wire is then drawn through the hole by using a microhook or the like. The end of the lead wire is then stripped of any coating and welded to the underside of the ring electrode, which is then slid into position over the hole and fixed in place with polyurethane glue or the like. Alternatively, each ring electrode is formed by wrapping a lead wire 30R around the non-conductive tubing 24 a number of times and stripping the lead wire of its own insulated coating on its outwardly facing surfaces.

The tip electrode 17 is electrically connected to a source of ablation energy (not shown) by the lead wire 30T. The ring electrodes 21 are electrically connected to an appropriate mapping or monitoring system by respective lead wires 30R.

The lead wires 30T and 30R pass through the lumen 27 (FIG. 3) of the tubing 19 of the deflectable intermediate section 14 and the central lumen 18 of the catheter body 12. The portion of the lead wires extending through the central lumen 18 of the catheter body 12, and proximal end of the lumen 27 can be enclosed within a protective sheath (not shown), which can be made of any suitable material, preferably polyimide. The protective sheath is anchored at its distal end to the proximal end of the intermediate section 14 by gluing it in the lumen 27 with polyurethane glue or the like. Each electrode lead wire has its proximal end terminating in a connector at the proximal end of the control handle 16.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. It is understood that the drawings are not necessarily to scale. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A catheter, comprising:
   an elongated catheter body;
   a tip electrode distal to the catheter body, the tip electrode comprising:
   a shell having a proximal neck portion and a distal chamber;
   a support member having a proximal portion and a distal portion, the proximal portion of the support member being inserted in the neck portion of the shell, and the distal portion of the support member extending into the chamber of the shell, the proximal portion of the support member having a fluid through-hole extending through an interior of the proximal portion of the support member; and
   a fluid channel provided between the neck portion of the shell and the distal portion of the support member, the fluid channel being on an outer surface of the distal portion of the support member and in fluid communication with the through-hole in the interior of the proximal portion of the support member, the fluid channel and through-hole defining a fluid flow path from the interior of the proximal portion of the support member to the fluid channel on the outer surface of the distal portion of the support member and to the distal chamber.

2. The catheter of claim 1, further comprising a position sensor at least partially housed in the distal portion of the support member.

3. The catheter of claim 1, wherein the fluid channel has a helical pattern on the outer surface of the support member.

4. The catheter of claim 1, wherein the fluid channel has axial and radial branches.

5. The catheter of claim 3, wherein the helical pattern extends at least about 360 degrees along a length of the distal portion of the support member.

6. The catheter of claim 3, wherein the helical pattern extends at least about 720 degrees along a length of the distal portion of the support member.

7. The catheter of claim 3, wherein the helical pattern extends at least about 1080 degrees along a length of the distal portion of the support member.

8. The catheter of claim 1, wherein the fluid channel has a proximal opening in communication with the through-hole in the interior of the support member, and a distal opening in communication with the distal chamber.

9. The catheter of claim 1, wherein the shell has a shell wall formed with fluid ports to allow fluid inside the distal chamber to flow to outside the distal chamber.

10. A catheter, comprising:
an elongated catheter body;
a tip electrode distal to the catheter body, the tip electrode comprising:
a shell having a distal chamber and a proximal neck portion; and
a support member having a proximal portion and a distal portion, the proximal portion being inserted in the neck portion and the distal portion extending into the chamber, the proximal portion having a fluid through-hole extending through an interior of the proximal portion of the support member, the distal portion having an outer surface facing an inner surface of the neck portion of the shell and a channel formed on the outer surface that provides a fluid passage between the fluid through-hole and the distal chamber, wherein the inner surface of the neck portion is adapted for exposure to fluid passing through the fluid passage.

11. The catheter of claim 10, further comprising a position sensor at least partially housed in the distal portion of the support member.

12. The catheter of claim 10, wherein the channel has a helical pattern on the outer surface of the distal portion of the support member.

13. The catheter of claim 10, wherein the channel has axial and radial branches.

14. The catheter of claim 12, wherein the helical pattern extends at least about 360 degrees along a length of the distal portion of the support member.

15. The catheter of claim 12, wherein the helical pattern extends at least about 720 degrees along a length of the distal portion of the support member.

16. The catheter of claim 12, wherein the helical pattern extends at least about 1080 degrees along a length of the distal portion of the support member.

17. The catheter of claim 10, wherein the channel has a proximal opening in communication with the through-hole and a distal opening in communication with the chamber.

18. The catheter of claim 10, wherein the catheter also has a connector tubing, a distal portion of which covers the neck portion, the neck portion and the distal portion of the connector tubing having aligned irrigation ports configured to allow irrigation fluid to pass from the channel to outside the neck portion and connector tubing to cool an outer surface of the connector tubing.

* * * * *